United States Patent [19]

Sandoval et al.

[11] Patent Number: 5,017,540
[45] Date of Patent: May 21, 1991

[54] SILICON HYDRIDE SURFACE INTERMEDIATES FOR CHEMICAL SEPARATIONS APPARATUS

[76] Inventors: Junior E. Sandoval, 812 S. Saratoga Ave., #Q111, San Jose, Calif. 95129; Joseph J. Pesek, 4142 Rosenbaum Ave., San Jose, Calif. 95136

[21] Appl. No.: 407,816

[22] Filed: Sep. 15, 1989

[51] Int. Cl.$^5$ ............................................. B01J 20/10
[52] U.S. Cl. ..................................... 502/158; 502/407; 423/341
[58] Field of Search ................. 423/325; 502/400, 407, 502/158

[56] References Cited

U.S. PATENT DOCUMENTS

| | | | |
|---|---|---|---|
| 2,705,222 | 3/1955 | Wagner | 252/188.26 |
| 3,839,385 | 10/1974 | Meiller et al. | 502/158 |
| 3,950,269 | 4/1976 | Setterquist | 502/154 |
| 3,956,179 | 5/1976 | Sebestian et al. | 502/158 |
| 4,257,916 | 3/1981 | Hancock et al. | 502/60 |
| 4,324,873 | 4/1982 | Wada et al. | 502/158 |
| 4,335,022 | 6/1982 | Slaugh | 502/263 |
| 4,467,048 | 8/1984 | Johnson | 502/246 |
| 4,555,395 | 11/1985 | Sirovich et al. | 423/644 |
| 4,661,248 | 4/1987 | Ramsden et al. | 210/198.2 |
| 4,680,201 | 7/1987 | Hjerten | 427/230 |
| 4,701,430 | 10/1987 | Jung et al. | 502/159 |
| 4,705,725 | 11/1987 | Glajch et al. | 502/407 |
| 4,746,572 | 5/1988 | Glajch et al. | 502/407 |
| 4,904,632 | 2/1990 | Pesek et al. | 502/401 |

FOREIGN PATENT DOCUMENTS 215884 11/1965 U.S.S.R. ............................ 556/430

OTHER PUBLICATIONS

Deuel et al., "119. Organische Derivative des Silikagels mit Si-O-C-Bindung I", *Helvetica Chimica Acta*, vol. 42, No. 119, pp. 1160–1165, 1959.
Slinyakova et al., "Adsorption and Other Properties of a Hydrogen-Silica Adsorbent with Si-H Bond (Polysiloxane Hydride Xerogel)", *Kolloidn. Zh.*, vol. 27, No. 5, pp. 758–764, 1965. (English abstract/translation provided.)
Budkevich et al., "Reduction Properties of Hydridepolysiloxane Xerogel", *Kolloidn. Zh.*, vol. 28, No. 1, pp. 21–26. (English abstract provided).
Slinyakova et al., "An Investigation of Adsorptive Properties of Ethylphenyl and Hydridopolysiloxanes by Gas Chromatography", *Ukr. Khim. Zh.*, vol. 33, No. 4, pp. 373–376, 1967 (English abstract provided.)
Kol'tsov et al., "The Effect of the Degree of Dehydration of Silica Gel on the Mechanism of Hydrolysis of Trichlorosilane", *Russian Journal of Physical Chemistry*, vol. 41, No. 3, pp. 336–337, Mar. 1967.
Morterra et al., "Reactive Silica. I. The Formation of a Reactive Silica by the Thermal Collapse of the Methoxy Groups of Methylated Aerosil", *J. Phys. Chem.*, vol. 73, No. 2, pp. 321–326, Feb. 1969.
Morterra et al., "Reactive Silica. II. The Nature of the Surface Silicon Hydrides Produced by the Chemisorption of Hydrogen", *J. Phys. Chem.*, vol. 73, No. 2, pp. 327–333, Feb. 1969.
Halasz et al., "New Stationary Phase for Chromatography", *Angew. Chem. Internat. Edit*, vol. 8, No. 6, pp. 453–454, 1969.

(List continued on next page.)

*Primary Examiner*—Anthony McFarlane
*Attorney, Agent, or Firm*—Majestic, Parsons, Siebert & Hsue

[57] ABSTRACT

The present invention produces very stable, covalently bonded separation substrates for separations application such as liquid and gas chromatography as well as capillary zone electrophoresis. An intermediate substrate is prepared which has hydride species on the substrate surface. These hydrides preferably are further derivatized by the catalytic addition of organic compounds bearing a terminal vinyl group. The final surface modification contains closely packed, direct carbon linkages that are stable.

8 Claims, 4 Drawing Sheets

OTHER PUBLICATIONS

Budkevich et al., "Adsorption of Various Substances from Their Solutions in Hexane and Carbon Tetrachloride on Hydride-Polysiloxane Xerogel and Silica Gel", *Kolloidn. Zh.*, vol. 32, No. 1, pp. 17–23, 1970. (English abstract.)

Budkevich et al., "Thermooxidative Degradation of Hydridopolysiloxane Xerogel", *Ukr. Khim. Zh.*, vol. 37, No. 5, pp. 429–433, 1971. (English abstract provided.)

Kurennaya et al., "Effect of an Acid Catalyst on the Porous Structure of Polyhydrosiloxane Xerogels", *Kolloidn. Zh.*, vol. 37, No. 1, pp. 178–181, 1975. (English abstract and translation provided.)

Asmus et al., "Preparation and Chromatographic Evaluation of Chemically Bonded Ion-Exchange Stationary Phases", *Journal of Chromatography*, vol. 123, pp. 109–118, 1976.

Roumeliotis et al., "Structure and Properties of n-Alkyldimethylsilyl Bonded Silica Reversed-Phase Packings", *Journal of Chromatography*, vol. 149, pp. 211–224, 1978.

Speier, "Homogeneous Catalysis of Hydrosilation by Transition Metals", *Advances in Organometallic Chemistry*, vol. 17, pp. 407–447, 1979.

Jorgenson et al., "Capillary Zone Electrophoresis", *Science*, vol. 222, pp. 266–272, Oct. 21, 1983.

Kirkland et al., "Liquid Phase Separation Methods: HPLC, FFFF, Electrophoresis", *Chromatographia*, vol. 24, pp. 58–76, 1987.

Sandoval et al., "Synthesis and Characterization of a Hydride-Modified Porous Silica Material as an Intermediate in the Preparation of Chemically Bonded Chromatographic Stationary Phases," *Analytical Chemistry*, vol. 61, No. 18, pp. 2067–2075, Sep. 15, 1989.

SILICON HYDRIDE SURFACE INTERMEDIATES FOR CHEMICAL SEPARATIONS APPARATUS

FIELD OF THE INVENTION

This invention relates to a surface-modified material used in a variety of separation applications, such as chromatography or electrophoresis.

More particularly, the invention pertains to a chemically modified mineral oxide, such as silica or quartz, which exhibits improved hydrolytic stability, larger organic coverage and superior separative capabilities when formed into various forms or shapes, such as porous beads or capillary tubes.

BACKGROUND OF THE INVENTION

Chemically modified silicas have been, and continue to be, widely used as supports in a great variety of chromatographic separations. With the aim of controlling its selectivity while reducing unwanted interactions with one or more compounds, numerous synthetic procedures have been developed to attach organic moieties (R) on the silica surface. Early work on the chemical modification of silica described the use of an esterification reaction between surface silanol groups and an alcohol to give Si-O-C linkages (Halasz and Sebastian, *Angew. Chem.* (Int. Ed.) 8:453 (1969); Deuel, et al., *Helv. Chim. Acta* 119:1160 (1959)). Although such materials were useful for many separations, their limited hydrolytic stability seriously precluded the extensive usage of these bonded phases, particularly in liquid chromatography which requires the use of aqueous eluents.

Currently, commercially available bonded phases are prepared by reacting selected organosilanes with the silica surface. Halogen- or alkoxy-substituted alkyldimethylsilanes react with the surface silanols attached to the silica surface through an Si-0-Si-C linkage. By using this approach it is possible to produce bonded silicas with a great variety of organic groups, ranging from non-polar materials, for instance, octyl- and octadecyl-silicas (R —$(CH_2)_nCH_3$, with n-7 and 17 respectively) commonly used as bonded supports in reversed-phase liquid chromatography, to ionic materials such as benzenesulphonic acid derivatives, which are widely used in ion-exchange liquid chromatography. The preparation of these and similar materials are described in a number of publications (e.g., Roumeliotis and Unger, *J. Chromatogr.* 149:211 (1978) or Asmus, et al., *J. Chromatogr.* 123:109 (1976)) and patents (Sebastian, et al., U.S. Pat. No. 3,956,179; Hancok, et al., U.S. Pat. No. 4,257,916; or Ramsden, et al., U.S. Pat. No. 4,661,248).

The new development of electrophoretic separations in a capillary format has promoted the extent of the silane technology normally used in chromatography to the deactivation of the inner wall of the quartz capillary. Thus, Jorgenson, et al. (Science 222:266 (1983)) have noted that separation of model proteins, such as cytochrome, lysozyme and ribonuclease A, in untreated fused silica capillaries with a phosphate buffer at pH 7 was accompanied by strong tailing, and suggested that this might be caused by strong interactions of the proteins and the capillary wall. Derivatization of the capillary wall has been proven effective to prevent or control protein sorption. In another application (U.S. Pat. No. 4,680,201 issued 1987), Hjerten describes a method for preparing a thinwall, capillary tube for electrophoretic separations by use of a bifunctional compound in which one group (usually a terminal —$SiX_3$ group where X=Ethoxy, methoxy or chloride) reacts with the glass wall and the other (usually an olefin group) does so with a monomer taking part in a polymerization process. This process resulted in a wall-bonded, polymer-filled capillary useful for polyacrylamide gel electrophoresis. In addition, by chemically modifying the quartz surface of the capillary, operational variables such as the electroosmotic flow are said to be more amenable to control.

The extensive usage of these bonded materials in chromatography and capillary electrophoresis does not necessarily imply that they meet all requirements with respect to separation performance and stability. On the contrary, they are subject to serious effects arising primarily from a relatively limited organic coverage due to the "bulky" methyl groups of the silane reagent and from a still unsatisfactory hydrolytic stability, particularly under moderately acidic or slightly alkaline elution conditions. This limited surface coverage along with a hydrolytically labile organic layer both result in the exposure of a substantial number of surface silanols, groups which are known to be primarily responsible for the residual adsorption phenomena that plague silicon-based materials. These so called "silanophilic" interactions are usually undesirable in chromatography as well as in capillary electrophoresis because they often result in "tailing" peaks, catalyzed solute decomposition, lead to unreliable quantitation, etc. One of the most striking cases of silanophilic interactions occurs perhaps in the separation of certain compounds containing amino or other similar groups, particularly biomolecules. For instance, many proteins may interact very strongly with unreacted silanols leading to excessive band tailing, incomplete recovery of one or more solutes, or even recovery of the same component from different bands. As a result of such problems, other organosilane reagents have been developed.

Two related approaches have been proposed in which the methyl groups of the organosilane reagent are replaced either by a "bidentate" or by a bulkier group (Kirkland and McCormick, Chromatographia 24:58 (1987)). In both cases the new groups are aimed to shield the unreacted silanols as well as the hydrolytically labile linkage that bonds the silane to the support. Although this steric protection has resulted in somewhat improved bonded phases, the necessity still exists for a truly effective silane chemistry.

In another completely different approach, bonded silicas bearing direct Si-C linkages have been developed. They involve the sequential reaction of the silica substrate with a chlorinating reagent (e.g., thionyl chloride) and a proper alkylating reagent (e.g., a Grignard or organolithium compound). In principle this method should provide not only a closer attachment and a denser coverage of organic functionalities but also a more hydrolytically stable bonded phase than that obtained by the corresponding Si-O-Si-C linkage. Nevertheless, the application of chlorination/Grignard or chlorination/organolithium reaction sequence to modify silica substrates has been hindered by several factors. One factor is that the one-step organosilanization (such as described in U.S. Pat. No. 3,956,179 to Sebastian, et al.) is relatively easy to produce materials as compared to the two-step halogenation/alkylation which, additionally, demands rigorous moisture-free conditions. Difficulties associated with the removal of residual salts which may be occluded in the porous silica matrix during the alkylation process is also an important factor which has contributed to the limited usage of this synthetic approach. Additionally, the preparation of the alkylation reagent exhibits strong interferences with many reactive functionalities, particularly those containing carbonyl, nitrile, carboxyl, amide, alcohol, etc. That is, the great reactivity which makes a Grignard reagent so useful in many synthetic approaches seriously limits its applicability. The organic group, R, in the Grignard reagent, RMgBr, must remain intact during the preparation of the reagent. It is a well known fact that Grignard reagents react with acidic components to form the corresponding hydrocarbon group R-H. More strictly, "any compound containing hydrogen attached to an electronegative element such as oxygen, nitrogen, and even triply-bonded carbon are acidic enough to decompose a Grignard reagent" (Morrison and Boyd, *Organic Chemistry*, 3rd Edition, 1974). Additionally, a Grignard reagent reacts readily with molecular oxygen, carbon dioxide, and with "nearly every organic compound containing a carbonoxygen or carbon nitrogen multiple bond" (supra). The group nitro ($-NO_2$) also appears to react oxidatively with a Grignard reagent. It seems clear therefore that only a very limited number of organic functionalities may be present in the halide compound from which a Grignard reagent can be prepared. Being even more reactive than the corresponding Grignard reagent, an organolithium reagent should exhibit the same limitations described above in a similar or greater extent. This, of course, greatly limits the versatility of this approach.

It is therefore desirable to address the shortcomings of existing bonded packings by developing an alternate silane chemistry which combines the superior coverage and hydrolytic stability of direct Si-C linkages with the preparation simplicity of silane derivatization.

SUMMARY OF THE INVENTION

In one aspect of the invention, a surfacemodified material is produced comprising an inorganic oxide substrate (such as silica, quartz or alumina). The surface of this material, or substrate, has been chemically modified. The chemical modification is whereby hydride species are formed. These hydride species can then be further reacted. When further reacted, the substrate surface is thus chemically modified so as to bear a variety of functionalities covalently attached to the support, through hydrolytically stable surface-to-carbon linkages.

In another aspect of the invention, a method for modifying the surface of an inorganic oxide substrate is provided, comprising two major steps: (1) attachment of hydride species on the substrate so as to give a relatively stable intermediate; and (2) reacting said hydrided surface with organic compounds bearing a terminal vinyl group, in the presence of a catalyst, whereby direct linkage of said inorganic substrate to carbon is provided.

It is a primary purpose of this invention to provide a surface-modified separation material which exhibits extended lifetime (hydrolytically stable), displays improved adsorption properties (larger and more versatile organic coverage), and is substantially free of contaminants (e.g., residual salts and the like).

The method of making this surface-modified material is a very versatile in that it provides an effective means of attaching organic functionalities to an inorganic substrate which otherwise cannot be introduced by regular organometallic procedures. Thus, the present invention provides a method suitable to prepare bonded substrates having direct carbon-substrate linkages whose organic part includes functionalities that otherwise could not be present in the organic part of Grignard or organolithium reagents. Thus, compounds having a hydrogen attached to oxygen, nitrogen and to a triply-bonded carbon, compounds containing a carbonoxygen and carbon-nitrogen multiple bond, and compounds containing a nitro group can be used to modify substrates in accordance with the invention, where such compounds would be foreclosed were Grignard and organolithium reagents to be utilized in the method.

The present invention represents a totally different approach to the prior problems in producing very stable, covalently bonded separation substrates for all types of liquid and gas chromatography as well as capillary electrophoresis. The new procedure involves the preparation of an intermediate which provides silicon hydride species on the silica surface, followed by the catalytic addition of such silicon hydrides to organic compounds bearing a terminal vinyl group. The final product contains closely packed direct Si-carbon linkages, thus providing a significantly improved surface-modified separation substrate with regard to stability and silanophilic interactions. Additionally, because of the intrinsic freedom from interferences of the catalytic SiH addition (also known as hydrosilation or hydrosilylation), the method of preparation is an extremely versatile one in that it allows bonding of virtually any organic functionality to a support material, in a clean, high-yield procedure.

DETAILED DESCRIPTION OF THE PREFERRED EMBODIMENTS

This invention differs from most of the methods currently available by using a direct substrate-to-carbon bond instead of a substrate-O-Si-C type of linkage. This invention describes a unique process which involves the catalytic addition of surface hydride species to an organic reagent containing a double bond, after converting the original surface hydroxyl to hydride groups. By contrast to other procedures, this invention requires neither additional post-reaction (end-capping) treatment, nor extensive clean-up procedures.

In one preferred embodiment, the substrate material to be modified according to the method described herein is silicon oxide in the form of silica, quartz or the like materials. These oxides are commonly used in gas and liquid chromatographic, as well as in capillary electrophoretic, separations. Alternative suitable substrates include other inorganic oxides, such as alumina, thoria, magnesia and combinations thereof. In a particularly preferred embodiment, the substrates to be modified are porous, particulate silica (such as beads) as well as nonporous quartz capillary tubes.

The modification method of the present invention comprises two major steps. One of the inorganic oxides as described above is provided; such a material provides a surface bearing hydroxyl groups. These hydroxyl groups provide active sites which can be chemically transformed into hydride groups. This is accomplished either by direct conversion of the hydroxyl groups to hydride groups (via a chlorination/reduction sequence) or by condensation of the surface hydroxyl groups with a hydridosilane coupling reagent. In either case, a chemically and thermally stable hydrided intermediate is obtained in which most of the original hydroxyl groups are replaced by silicon hydride species. In the second major step, the hydrided surface is reacted with an organic compound containing a double bond, preferentially a terminal vinyl group, in the presence of an appropriate catalyst so as to give a direct linkage of the surface to carbon.

One procedure to prepare the hydride intermediate material via the halogenation/reduction sequence is as follows. A predetermined quantity of inorganic oxide substrate, e.g., silica, is added to an anhydrous solvent such as toluene and a suitable excess of a halogenating reagent is added thereto, preferably thionyl chloride. The reaction is allowed to proceed under a nitrogen atmosphere at reflux for 18–24 hours, at which point the halogenated solid is isolated, washed and dried. Reduction is effected by slowly adding the halogenated material to a suitable excess of an ethereal solution of an inorganic hydride such as lithium aluminum hydride. The reaction is carried out in a reactor equipped with a condenser containing a suitable frigorific mixture such a dry ice/acetone. The reduction is allowed to proceed at room temperature for about 3–5 hours, under nitrogen atmosphere. The reduced material is finally subjected to a "clean-up" step so as to remove contaminating salts (e.g., aluminum chloride) from the reducing reagent. The solid is washed several times with diluted aqueous acid, after which the product is rinsed with water and a suitable alcohol such as methanol. The solid then dried at high temperature for several hours, typically at 110° C. overnight (see Example 1).

One alternate procedure to prepare the hydride intermediate is as follows: A predetermined quantity of inorganic oxide substrate, e.g., silica, is added to a dilute alcoholic mineral acid solution (typically a 0.1M HCl solution in 95% ethanol) and a suitable excess of a hydridosilane agent is added thereto, preferably a trialkoxysilane or trihalosilane such as triethoxysilane or trichlorosilane. The reaction is allowed to proceed for several hours (typically 2–6 hours), at which point the hydrided material is isolated and washed with alcohol (see Example 5).

Catalytic hydrosilation of olefins on the hydrided substrate is carried out as follows. A predetermined quantity of hydride intermediate prepared as described above is added to a suitable excess of solution of the olefin in a preferably anhydrous solvent such as toluene or chloroform. No solvent is usually required with liquid olefins. The olefin solution also contains an amount of catalyst complex so that an approximate $1:10^4$ molar ratio of catalyst to hydride is attained. The reaction is allowed to proceed for 18–24 hours at elevated temperature, typically 80–100° C., at which point the bonded material is isolated and washed (see Examples 6 and 7). Depending upon the desired product, the olefin reagent is selected from a large number of organic compounds, preferably those bearing a terminal vinyl group, i.e., those with the general formula $CH_2=CH-R$ where R ranges from simple hydrocarbon groups such as n-alkyls, to heteroatom compounds such as carbonyls, nitriles, amides, etc.

Because of easy availability, chloroplatinic acid is the preferred catalyst used, usually in a 2-propanol solution. However, other transition metal complexes can be used with similar results.

Thus, the present invention provides a surfacemodified material comprising an inorganic oxide that originally had surface hydroxyl groups. These surface hydroxyl groups are chemically modified so as to provide a covalently bonded organic layer having a plurality of functionalities. Among the functionalities that may be present in the covalently bonded organic layer (where the bonding is by means of a direct carbon-substrate linkage) are where a hydrogen is attached to oxygen, nitrogen and to a triply-bonded carbon, where there is a carbon-oxygen and carbon-nitrogen multiple bond, and where there is one or more nitro groups. The inorganic oxide material preferably is selected from oxides of silicon, aluminum, zirconium, tin, titanium, and combinations thereof. Suitable substrates include quartz and particulate silica.

Where silica is selected, then the silica may be porous (such as a column packing material suitable for gas and liquid chromatography) or non-porous (such as a non-porous capillary tube). Porous silicas preferably have a surface area of at least about 100 $m^2/g$ and an average pore diameter of about 60 Å, although surface areas can be in the range of about 50 to a few hundred $m^2/g$ and pore diameters can range from 30 to about 500 Å. Non-porous capillary tubes typically have an inner diameter less than about 500 $\mu$, more typically between about 20 $\mu$ to about 200 $\mu$.

Whether porous or non-porous, the inorganic oxide substrates are preferably rigid and noncollapsible structures since, for example, column packing materials often must withstand pressures that can be on the order of several thousand psi and capillary tubes require structural integrity.

In accordance with the invention, the surface hydroxyl groups initially present on the inorganic oxide substrate are reacted so as to give an intermediate material containing surface hydride groups. This reacting step may be performed by either one of two procedures. One procedure is a halogenation/reduction sequence. The other procedure is a single silane coupling reaction. The halogenation/reduction sequence comprises halogenation of the inorganic oxide substrate followed by reduction of the halogenated material and preferably by post-reaction treatment with aqueous acid. Such halogenation is preferably accomplished with a chlorinating reagent. A particularly preferred chlorinating reagent is thionyl chloride, although other suitable chlorinating reagents include but are not limited to $SiCl_4$, $S_2Cl_2$, $Cl_2CO$, $CCl_4$ and $CH_3COCl$. The halogenated material, or moieties, are then reacted with an inorganic hydride. Suitable inorganic hydrides include aluminum hydrides, boron hydrides, and the like.

If a single silane coupling reaction is selected as the procedure in accordance with the invention, then the coupling reagent preferably is a hydridosilane of the formula $H_nSiX_{4-n}$ where X is a hydrolyzable group, and n is an integer in the range of 1 and 3. Particularly preferred such hydride silane coupling reagents are triethoxysilane and trichlorosilane.

These solid intermediates so obtained are then further derivatized. The further derivatization is preferably by reacting the intermediate hydrides with an olefin reagent in the presence of a catalyst whereby direct linkage to carbon is obtained.

As previously known in other contexts, the addition of silicon hydrides to alkenes is one of the most important laboratory methods to form Si-C bonds. The reaction's minimal interferences with other reactive functionalities (e.g., $CO_2R$, $NH_2$, etc.) has permitted the attachment of silicon to organic molecules which otherwise cannot be introduced by regular organometallic procedures. Hydrosilation is generally carried out in the presence of a transition metal catalyst. A variety of inorganic and organic complexes of platinum, rhodium, palladium, ruthenium, iridium and nickel have functioned as very effective catalysts for the addition reaction. Chloroplatinic acid in an isopropanol solution (also known as "Speiers" catalyst) is the most commonly used form. Only as little as $10^{-3 \text{ to } 5}$ mole of platinum per mol of silicon hydride is normally required for an effective hydrosilation. The addition is rapid and can be done at room temperature or under reflux to ensure a high yield. Details of the reaction in homogeneous phase can be found elsewhere (e.g., Speier, *Adv. Organomet. Chem* 17:407 (1979); Seyferth, editor, *J. Organomet. Chem. Library* 5:1 (1977)).

Among the advantages of practice of the invention are that the relatively limited organic coverage due to the "bulky" methyl groups of prior art organosilanes can be avoided and more hydrolytically stable surface modifications may be obtained. Additionally, the advantages of direct Si-C linkages may be achieved without the disadvantages that occur when obtained by the known sequential reaction with chlorinating reagent and an alkylating reagent such as Grignard. Thus, the present invention not only combines the superior coverage and hydrolytic stability of direct Si-C linkages with a simplicity approaching that of silane derivatization, but also dramatically increases the versatility of the attaching group.

A wide variety of compounds can be bonded through direct carbon-substrate linkages to substrates of the invention. A few illustrative examples include carboxylic acids and their derivatives, generally represented as where, for example, G is —OH, —Cl, —H or —NR$_2$ (with R being an alkyl or hydrogen) and n is 0 to quite large, but typically 10 to 20.

Use of amides (where G=NHR) is particularly suitable for affinity chromatography applications. Additionally, nitriles and imines are suitable, generally represented as $CH_2=CH-(CH_2)_n-C\equiv N$ and $CH_2=CH-(CH_2)_nC=NR$ where R and n are as above described.

Figure 1:
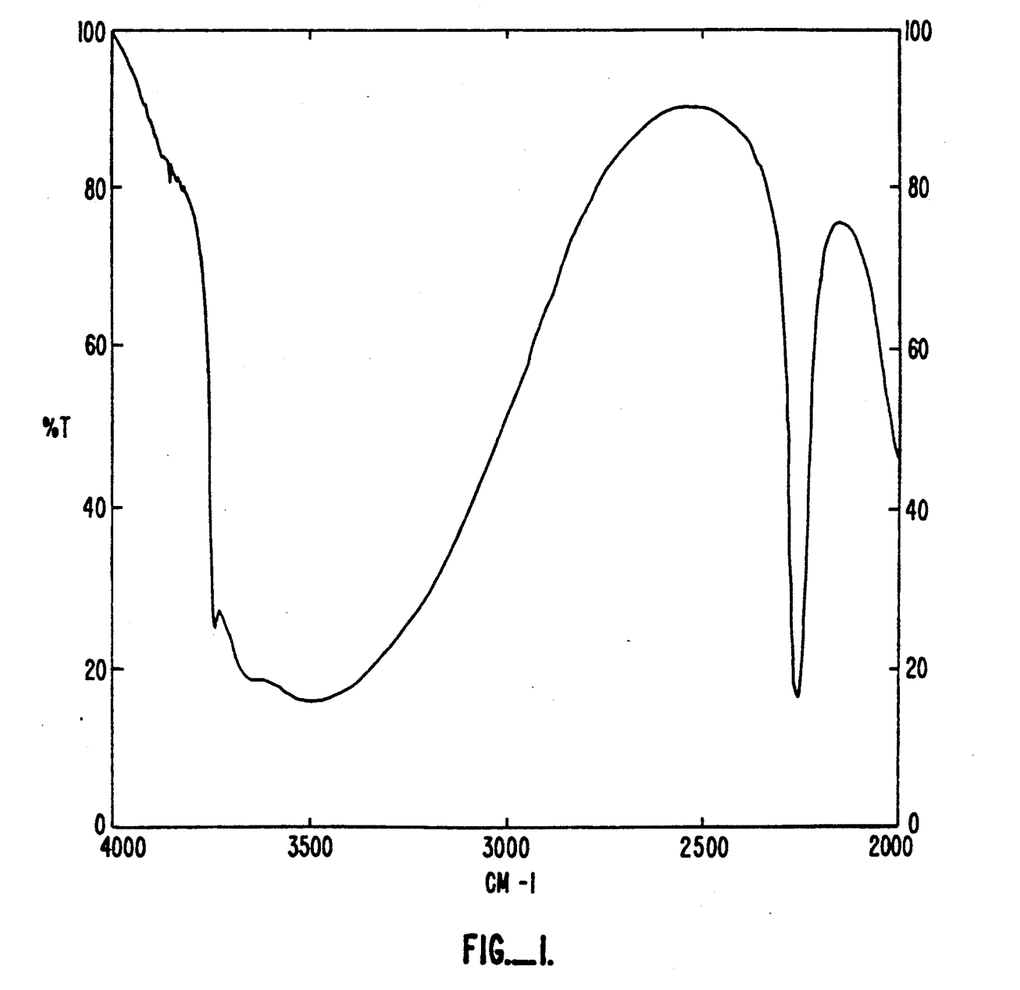
FIG. 1 illustrates a partial IR spectrum of a hydride intermediate embodiment.
Figure 2:
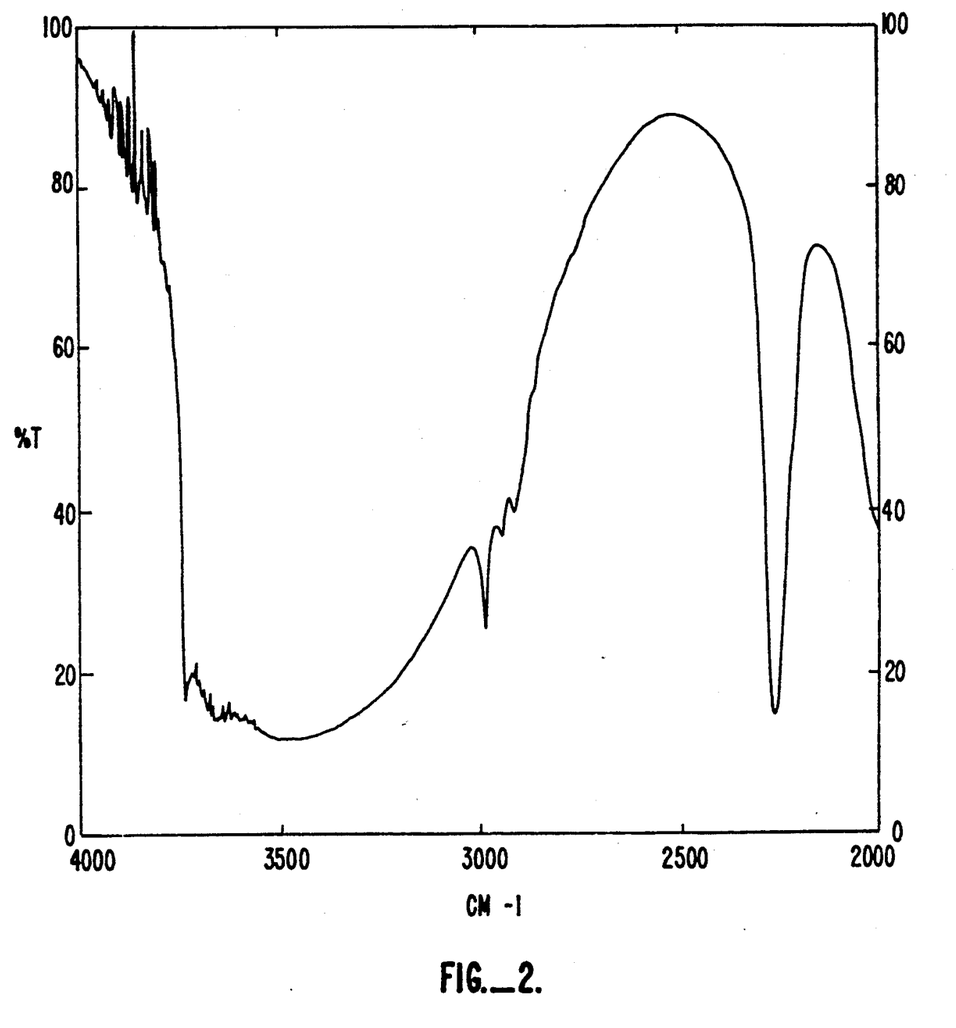
FIG. 2 illustrates a partial IR spectrum of another hydride intermediate embodiment.
Figure 3:
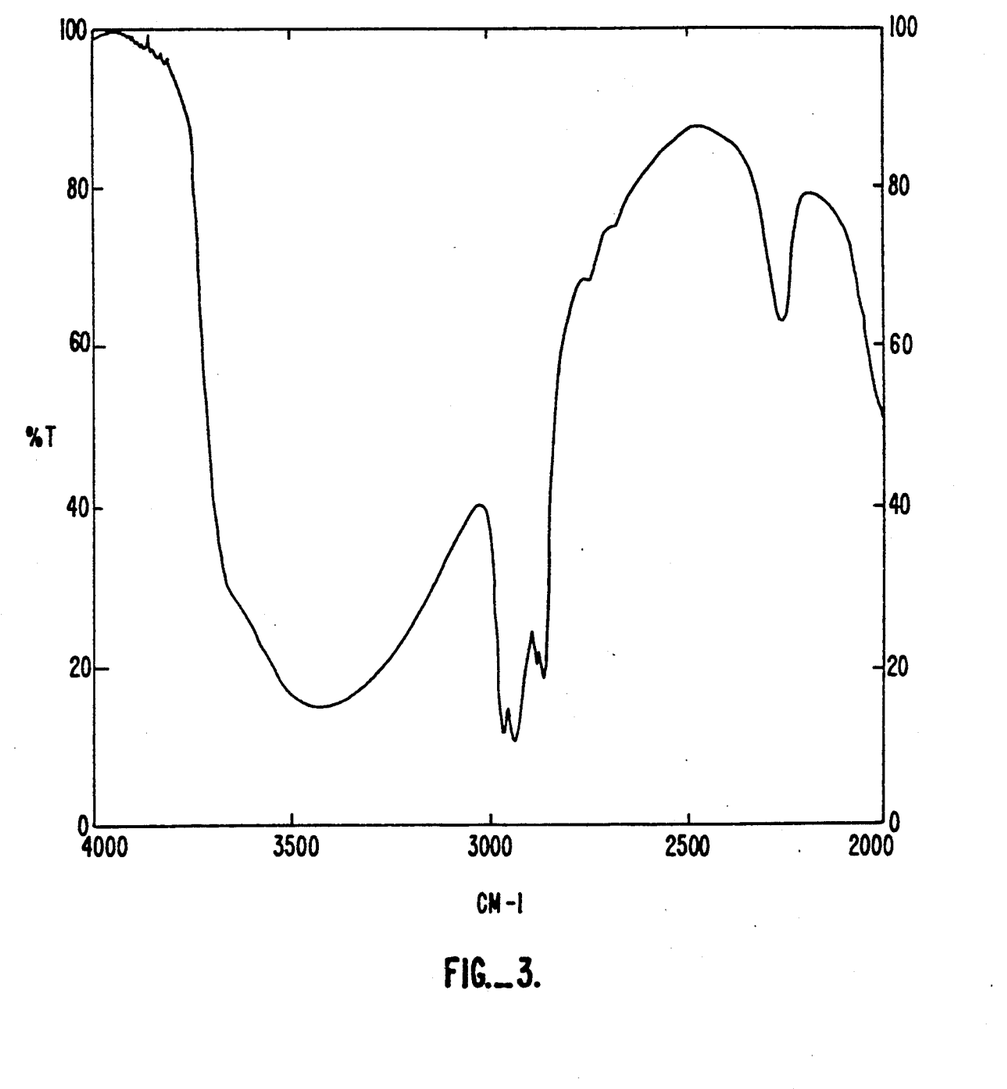
FIG. 3 illustrates a partial IR spectrum of an octyl-bonded silica embodiment.
Figure 4:
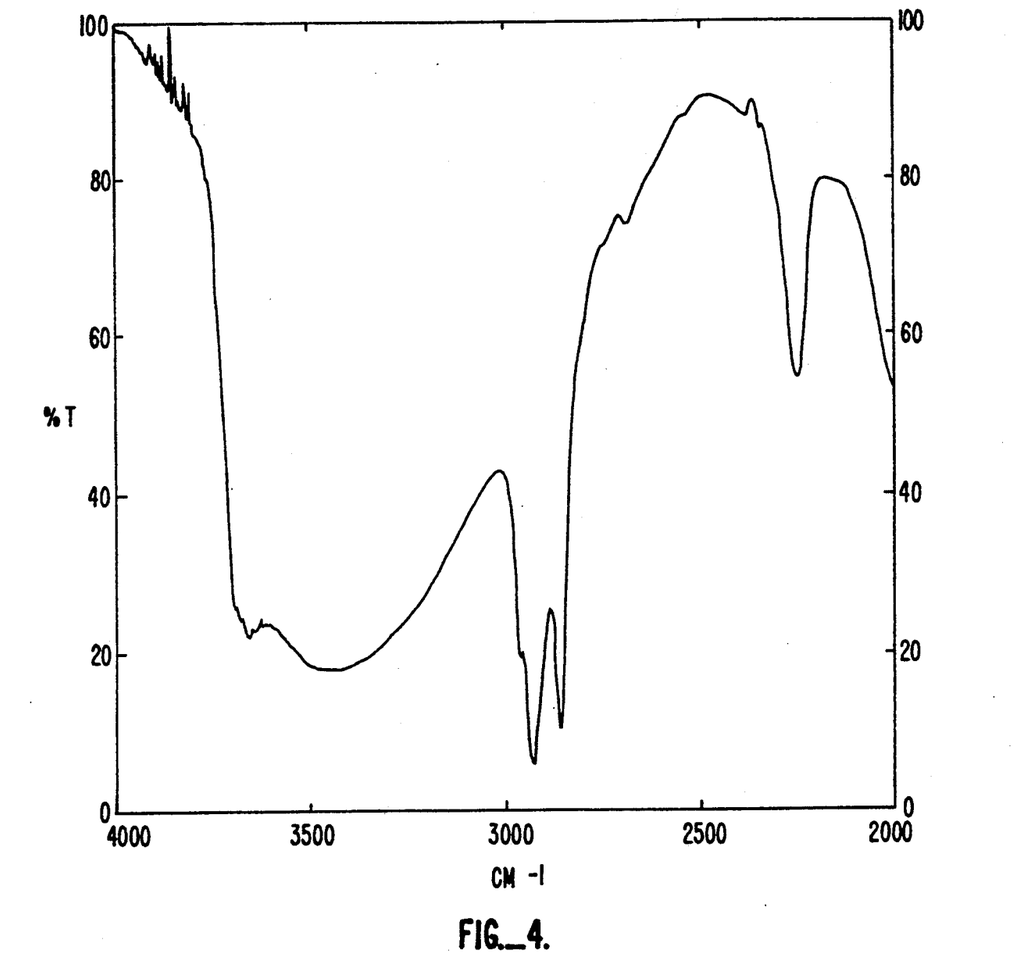
FIG. 4 illustrates a partial IR spectrum of an octadecyl-bonded silica embodiment.

Turning to the figures, FIG. 1 illustrates a partial IR spectrum of a hydride intermediate embodiment prepared via a chlorination/reduction sequence according to the invention, as will be further described in Example 1. FIG. 2 illustrates a partial IR spectrum of another hydride intermediate embodiment that was prepared via coupling of a porous silica with triethoxysilane in accordance with the invention, as described in Example 5. The spectrum of this material closely matches that of FIG. 1 which indicates that high conversion to the hydride is possible by using this single step procedure. FIG. 3 illustrates a partial IR spectrum of an octyl-bonded silica embodiment prepared according to the invention, as described by Example 6. FIG. 4 illustrates a partial IR spectrum of another octadecyl-bonded silica embodiment prepared according to the invention, as described in Example 7.

EXPERIMENTAL

Materials and Methods

Toluene and diethyl ether (EM industries, Inc.) were dried by allowing them to stand with calcium hydride (Sigma Chemical Co.) for several days, refluxing and then distilling from the hydride immediately before use. A 0.2M lithium tetrahydridoaluminate (Sigma Chemical Co.) ether solution was prepared and used as the reducing reagent. Thionyl chloride ("gold label", Aldrich Chemical Co.) was used as received. IR quality potassium bromide (Harshaw/filtrol Partnership) powder was used for the FT-IR spectra. Partisil-40 (Whatman Inc., Clifton, NJ) with a 40 nm mean particle size, 85 Å mean pore size and 350 m$^2$/g surface area (manufacturer's typical data) was used as the silica material.

All silica derivatization reactions were carried out under a dry $N_2$ atmosphere in glassware that had been previously dried at 120° C. overnight. The LiAlH ether solution was prepared in a $N_2$-flushed glovebag. Transfer of liquids was carried out either with a glass syringe (<20 ml) or by means of a stainless steel cannula and $N_2$-pressure, via silicone rubber septa. Prior to reaction, the silica was dried under vacuum at 120° C. overnight and then cooled in a vacuum desiccator.

Infrared spectra were taken in the 4000-450 cm$^{-1}$ region with a Perkin-Elmer Model 1800 FT-IR spectrometer equipped with a Spectra-Tech diffused reflectance accessory. Dried ground KBr was mixed with an equal amount (by weight) of silica material. Samples were filled into the accessory's cup by gently tapping until a small sample mound was formed. A very smooth sample surface was then obtained by pressing down a microscope slide onto the cup while moving it in a circular motion. Before taking a spectrum, the height of the sample cup was adjusted by using the alignment routine provided with the standard Perkin-Elmer software. This resulted in a reproducible positioning of the sample surface at the optimum height so that a maximum signal throughput was consistently obtained. Spectra were collected at a nominal resolution of 2 cm$^{-1}$ with a weak Norton-Beer apodization. 200 sample scans were ratioed against pure KBr as reference. Band intensities (absorbance units) for triplicate spectra of samples prepared in this manner had relative standard deviation equal or better than 7%. Spectra shown were normalized to 100% transmittance.

ESCA measurements were done with a surface Science Laboratories model SSX-01 spectrometer equipped with an Al K$\alpha$ x-ray excitation source. Spectra were obtained at an energy resolution of about 1 eV from a 600×1000 $\mu$m sample spot. Typically, the x-ray beam penetrated the top $\sim$100Å of selected silica samples.

Example 1

5.00 g (approximately 14 moles of silanol, assuming 4.6 groups per nm$^2$) of dried silica were suspended in 60 mL of freshly distilled, dry toluene, and 10.2 mL of thionyl chloride (about a 10-fold molar ratio excess with respect to silanol content) were added. The mixture was magnetically agitated and the chlorination was allowed to proceed under reflux for at least 18 hours after which the excess SOCl$_2$ was distilled off. Removal of any remaining SOCl$_2$ was carried out by washing the dark-purple product at least 8 times with 80-mL portions of dry toluene while magnetically stirring for 15 min. After each washing, and once the solid had settled, the solvent was carefully aspirated off to waste by means of a vacuum applied to a glass pipette. Finally, the chlorinated silica was washed with one 30-mL portion of dry diethyl ether, remaining in a final fresh ether aliquot.

70 mL of 0.2M LiAlH$_4$ ether solution (about a 4-fold molar ratio, hydride: original silanol) were added slowly to the chlorinated silica/ether suspension. An immediate reaction was evidenced by a color change from dark purple to white. The reaction was allowed to proceed for 2 hours under a gentle reflux. The excess of LiAlH$_4$ was aspirated off and destroyed by adding dry ethyl acetate (about 10 mL) followed by isopropanol dropwise with stirring until hydrogen evolution ceased. This also confirmed that an excess of the reducing reagent was present at the end of the reduction reaction. The product was next washed as described above with eight 30 mL portions of dry ether to remove any remaining aluminum hydride and/or chloride species in solution. The "reduced silica" was then dried overnight in a vacuum oven at 120° C.

EXAMPLE 2

The Si-H group is readily identified by a strong stretching band in the range 2300 to 2100 cm$^{-1}$, along with a relatively weak bending band between 760 and 910 cm$^{-1}$, the former being located in a region where the absorption due to the silica matrix is minimal. When chlorinated silica was reduced with an excess of LiAlH, a broad peak was produced at about 2280–2200 cm$^1$. The shape of the peak suggested a multiplet whose position is consistent with that of SiH species in which the silicon atom is bonded to several electronegative atoms. Although the multiplet may be attributed to more than one possible SiH species (namely —SiH and —Si(OH)H which originated from single and geminal silanols respectively), the formation of surface AlH (alane) species, which is also feasible under the reaction conditions, may also explain at least partially the low-frequency component of the broad absorption. Due to the excess of reducing reagent, the presence of unreacted silanols and the virtual absence of shielding effect from hydrogen atoms as the reduction of chlorinated silica progresses, the silanols become increasingly accessible to attack by the reducing reagent, believed to lead to the formation of surface alane species:

(1)

X = H, Cl    n = 1, 2, 3

This situation is contrary to that of most (if not all) silica derivatizations, in which the original surface species become progressively unaccessible to the modifier's attack. Slow but unequivocal gas evolution (X - H in the above reaction (1)) was observed after the reacting mixture was allowed to settle for several minutes and the reaction flask was gently tapped (in fact, gas evolution was more readily observed by using a much larger excess of reducing reagent). This observation is further substantiated by reacting a small amount of native (i.e., fully hydroxylated) silica with ethereal LiAlH. A relatively broad and asymmetrical peak at 2181 cm$^{-1}$, very likely due to surface alane species formed through reaction (1), was obtained.

EXAMPLE 3

To investigate the hydrolytic stability of silane as well as alane surface species, small portions of reduced silica (chlorinated solid reacted with excess LiAlH$_4$) were treated with 0.01M NaOH, deionized water and 0.1M HCl. As evidenced from slow gas evolution and confirmed by IR spectra, treatment with aqueous alkali (pOH=2) resulted in the complete elimination of both alane as well as silane species while water (pOH=7) does so at a much slower rate. Acidic (pOH=13) treatment on the other hand resulted in the complete elimination of the low-frequency alane component of the originally broad band and, interestingly, a significant increase in the intensity of the 2260 cm$^{-1}$ Si-H band. The observed enhancement of the Si-H band intensity may be attributed to the effect of either or both of two factors: (i) the hydrolytic removal of IR active —Al—H species from the silica matrix which may cause an increase of the effective penetration of IR radiation and thus a more intense SiH absorption; and (ii) the formation of additional surface SiH species at the expense of adjacent alanes.

EXAMPLE 4

The ESCA technique can produce valuable information about many chemisorbed species present on the reduced silica surface, with the exception of hydrogen. Five consecutive 10-min. washings with aqueous HCl acid (10 mL of 0.5M solution per gram of solid) were carried out to thoroughly eliminated unwanted species present on the surface. This procedure was found efficiently to remove chemisorbed aluminum (characterized by two peaks with binding energies of 75 and 116 eV) from the untreated material down to the background levels of unreacted silica.

Curiously enough, traces of chemisorbed carbon (binding energy 281 eV) were also significantly found to be removed through acid treatment. Carbon chemisorption can be explained in terms of a secondary reaction (solvolysis) taking place during the reduction of chlorinated silica in ethereal medium. Subsequent removal of the carbonaceous species during acid treatment is consistent with the well known hydrolytic instability of the Si-0-C linkage.

Complete elimination of surface alanes from reduced silica is believed necessary in order to minimize the deactivation (via reduction) of a metal catalyst during the surface hydrosilation of terminal olefins. Treatment of the reduced material with aqueous acid should therefore be incorporated in the synthesis of the silica intermediate.

EXAMPLE 5

Five grams of silica (Partisil-40, 350 m$^2$/g) were suspended in 125 mL of 0.1M HCl solution in 95% ethanol with magnetic stirring, and 3.5 mL of triethoxy silane (about 30% molar excess with respect to silanol content) were added. The reaction was allowed to proceed at room temperature for about 30 minutes after which the suspension was centrifugated and the solid washed with five 50-mL portions of ethanol. The solid was filtered and finally dried at 110° C. under vacuum overnight.

The product obtained exhibited essentially identical spectroscopic, chemical and thermooxidative characteristics of that prepared via chlorination/ reduction sequence as described in Example 1. The simplicity and efficiency of this procedure make the hydridosilane coupling a preferred method.

EXAMPLE 6

Five grams of hydride intermediate substrate (e.g., that prepared as described by Example 1) are added to 60 mL of 1-octane (density 0.715 g/cc, 90% purity) containing 75 µL of 0.1M chloroplatinic acid solution in 2-propanol. The suspension was magnetically agitated and the reaction allowed to proceed for about 24 hours at 80±5° C. The mixture was then centrifugated and the solid washed with three 40-mL portions of toluene followed by similar was ings with dichloromethane. The solid was then filtered and finally dried at 110° C. overnight. The octyl-bonded silica contained 10.9% (by weight) of carbon, which corresponds to a surface coverage of about 3.7 µmole of octyl groups per square meter. The use of an equivalent amount of the olefin-platinum complex dicyclopentadienyl platinum(II) dichloride as catalyst resulted essentially in the same level of surface coverage. A partial IR spectrum of the product is shown in FIG. 3.

EXAMPLE 7

Five grams of hydride intermediate material (e.g., that prepared as described in Example 1) were suspended in about 60 mL of 1-octadecene (density 0.79 g/cc, 99% purity) containing 50 µL of a 0.2M solution of dicyclopentadienyl platinum (II) dichloride in dichloromethane. The mixture is agitated and the reaction allowed to proceed for about 24 hours at 90±5° C. after which the product is washed and dried as described in Example 6. The octadecyl-bonded silica contained 11.8% of carbon representing a surface coverage of about 1.8 µmole of octadecyl per square meter. This material represents another example of long-chain olefin hydrosilylation on a hydride-derivatized support. Similar results are obtained when chloroplatinic acid is used as catalyst. A partial IR spectrum of the product is shown in FIG. 4.

It is to be understood that while the invention has been described above in conjunction with preferred specific embodiments, the description and examples are intended to illustrate and not limit the scope of the invention, which is defined by the scope of the appended claims.

It is claimed:

1. A method for modifying the surface of an inorganic oxide substrate useful for chromatography or electrophoresis separations comprising:
   converting surface hydroxyl groups of said substrate to intermediate surface hydride groups; and
   reacting said intermediate surface hydride groups with an olefin reagent in the presence of a catalyst to form a reaction product thereof on the surface of the substrate, the reaction product having carbon atoms of the olefin reagent directly linked to the surface of the substrate.

2. The method of claim 1 wherein the converting is either by means of a halogenation/reduction sequence or by means of a single silane coupling reaction.

3. The method of claim 2, wherein said halogenation/reduction sequence comprises halogenation of the inorganic oxide substrate followed by reduction of the halogenated material and then post-reaction treatment with aqueous acid.

4. The method of claim 3, wherein said halogenation comprises reaction with a chlorinating reagent.

5. The method of claim 3, wherein said reduction comprises reaction of the halogenated material with an inorganic hydride.

6. The method of claim 5, wherein said inorganic hydride includes aluminum hydrides or boron hydrides.

7. The method of claim 2, wherein said silane coupling reaction comprises reaction of the inorganic oxide substrate with a hydrosilane coupling reagent of the formula $H_nSiX_{4-n}$ where X is a hydrolyzable group, and n is an integer in the range of one and three.

8. The method of claim 7, wherein said hydrosilane coupling reagent includes triethoxysilane or trichlorosilane.

* * * * *